United States Patent
Shaikh et al.

(10) Patent No.: US 9,856,335 B2
(45) Date of Patent: *Jan. 2, 2018

(54) PRODUCTION OF HIGHLY REACTIVE LOW MOLECULAR WEIGHT PIB OLIGOMERS

(71) Applicant: TPC Group LLC, Houston, TX (US)

(72) Inventors: Sohel K. Shaikh, Dhahran (SA); Rex Lawson, Pearland, TX (US)

(73) Assignee: TPC GROUP LLC, Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 15/238,092

(22) Filed: Aug. 16, 2016

(65) Prior Publication Data

US 2016/0355620 A1    Dec. 8, 2016

Related U.S. Application Data

(62) Division of application No. 14/118,254, filed as application No. PCT/US2012/040897 on Jun. 5, 2012, now Pat. No. 9,453,089.

(Continued)

(51) Int. Cl.
   *C08F 110/10* (2006.01)
   *C08K 5/13* (2006.01)
   *C07C 2/20* (2006.01)

(52) U.S. Cl.
   CPC .............. *C08F 110/10* (2013.01); *C07C 2/20* (2013.01); *C08K 5/13* (2013.01); *C07C 2527/1213* (2013.01)

(58) Field of Classification Search
   CPC ............ C08F 110/10; C08K 5/13; C07C 2/20
   See application file for complete search history.

(56) References Cited

U.S. PATENT DOCUMENTS

| | | |
|---|---|---|
| 3,721,661 A | 3/1973 | Susa |
| 3,808,187 A | 4/1974 | Steigerwald et al. |

(Continued)

FOREIGN PATENT DOCUMENTS

| | | |
|---|---|---|
| DE | 2118869 A1 | 10/1972 |
| DE | 4231748 A1 | 3/1994 |

(Continued)

OTHER PUBLICATIONS

J. P. Kennedy et al, Carbocationic Polymerization (1982), p. 229, John Wiley & Sons, New York.

(Continued)

*Primary Examiner* — Catherine S Branch
(74) *Attorney, Agent, or Firm* — Michael W. Ferrell (57) ABSTRACT

In one preferred embodiment, the present invention provides a process for the liquid phase polymerization of isobutylene to manufacture highly reactive PIB oligomers having Mn under 1000, using a catalyst composition comprising a Friedel-Crafts catalyst a complexing agent, a chain transfer agent and a polymerization-retarding agent. A chain transfer agent may be selected from: α-DIB and β-DIB and mixtures thereof.

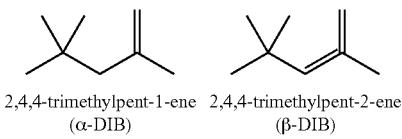

2,4,4-trimethylpent-1-ene (α-DIB)    2,4,4-trimethylpent-2-ene (β-DIB)

A polymerization-retarding agent may be selected from:

(Continued)

US 9,856,335 B2

Page 2

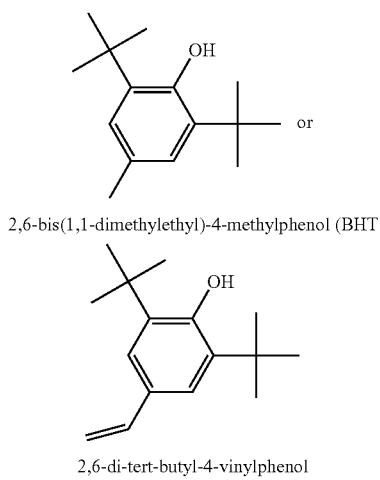

2,6-bis(1,1-dimethylethyl)-4-methylphenol (BHT 2,6-di-tert-butyl-4-vinylphenol

20 Claims, 4 Drawing Sheets

Related U.S. Application Data (60) Provisional application No. 61/586,206, filed on Jan. 13, 2012, provisional application No. 61/520,328, filed on Jun. 8, 2011.

(56) References Cited

U.S. PATENT DOCUMENTS

| 4,097,464 | A  | 6/1978  | Kline            |
| 5,157,164 | A  | 10/1992 | Olivier          |
| 5,378,779 | A  | 1/1995  | Fauth et al.     |
| 5,556,932 | A  | 9/1996  | Rath et al.      |
| 5,883,196 | A  | 3/1999  | Rath et al.      |
| 5,962,604 | A  | 10/1999 | Rath             |
| 6,683,138 | B2 | 1/2004  | Baxter, Jr. et al. |
| 6,710,140 | B2 | 3/2004  | Wettling et al.  |
| 6,852,808 | B2 | 2/2005  | Hüffer et al.    |
| 8,016,898 | B1 | 9/2011  | Lange et al.     |
| 2003/0162918 | A1 | 8/2003 | Wettling et al. |
| 2003/0187173 | A1 | 10/2003 | Kaszas         |
| 2013/0324665 | A1 | 12/2013 | Shaikh et al.  |

FOREIGN PATENT DOCUMENTS

| EP | 0154164 A2     | 9/1985  |
| EP | 0452875 A1     | 10/1991 |
| JP | 63205305 A     | 8/1988  |
| JP | 05186513 A     | 7/1993  |
| JP | 06345821 A     | 12/1994 |
| MX | PA/a/2003/001130 A | 6/2003 |
| SU | 1016304 A1     | 5/1983  |
| SU | 1659424 A1     | 6/1991  |
| WO | 2002038630 A1  | 5/2002  |
| WO | 2005066222 A1  | 7/2005  |

OTHER PUBLICATIONS

Rooney, "Synthesis of Phenol-Terminated Polyisobutylene: Competitive Chain Transfer Reactions", Journal of Applied Polymer Science (1980) 1365-1372, vol. 25(7), John Wiley & Sons, Inc.
Priola, "Relative Reactivity of cis- and trans-1,3-Pentadiene in the Cationic Copolymerization with Isobutene", Die Makromolekulare Chemie (1975) 1969-1981, vol. 176(7).
Penfold et al, "Chain-transfer by Anisole in the Cationic Polymerisation of Isobutene", Proc. of the Chem. Soc. (London) (1961) 311-312.
W. Gunther et al, "Structural investigations on low-molecular-weight polyisobutylenes", Die Angewandte Makromoleculare Chemie (1996), pp. 71-90, vol. 234, Nr. 4084, Huthig & Wepf Verlag, Zug.
J. Spevacek et al, "13C NMR characterization of unsaturated terminal structures in oligoisobutylenes", Polymer Bulletin (1995), pp. 461-467, vol. 34, Springer-Verlag.
Byrikhin et al, "Termination reactions in polymerization of isobutylene in . . . ", Lomonosova (1975) 107-112, vol. 5(2).
Kennedy, et al., High Polymers, vol. XXIV (1971), pp. 692-693 and 712-719, J. Wiley & Sons, Inc., New York.
Kennedy, J.P. and Ivan, B., Designed Polymers by Carbocationic Macromolecular Engineering: Theory and Practice (1991), pp. 86-90 and 136-137, Hanser.
Prokofev et al, "The synthesis of high-molecular weight polyisobutylene in methyl chloride", Promyshlennost Sinteticheskogo Kauchuka (1982), 12-15, vol. 7 (Abstract, only).
Li et al., "Cationic Polymerization of Isobutylene Coinitiated by AlCl3 in the Presence of Ethyl Benzoate", Chinese Journal of Polymer Science (2010), pp. 55-62, vol. 28, No. 1, Chinese Chemical Society.
Kaszas et al., "Electron Pair Donors in Carbocationic Polymerization", Polymer Bulletin (1988), pp. 413-419, vol. 20, Issue 5, Springer-Verlag.
Russell et al., "Rates of Initiation of the Cationic Polymerization of Isobutene", Journal of Polymer Science (1976) pp. 183-189, Symposium No. 56, Issue 1, John Wiley & Sons, Inc.
Paul Grosso and Otto Vogl, "Functional Polymers. XLIII. Olefin Copolymers of 2,6-Di-t-butyl-4-vinyl (or 4-isopropenyl) phenol", Journal of Macromolecular Science: Part A—Chemistry: Pure and Applied Chemistry (1986), pp. 1299-1313, A23(11), Marcel Dekker, Inc.
J.P. Kennedy et al.,"Cationic Polymerization with Boron Halides. III. BCl3 Coinitiator for Olefin Polymerization", Journal of Polymer Science: Polymer Chemistry Edition (1977) pp. 2801-2819, vol. 15, John Wiley & Sons, Inc.
International Preliminary Report on Patentability dated Oct. 15, 2013 from the parent application, i.e., U.S. Appl. No. 14/118,254.
Written Opinion of the International Searching Authority dated Jan. 31, 2013 from the parent application, i.e., U.S. Appl. No. 14/118,254.
Supplementary European search report and European search opinion, dated Oct. 24, 2014, disclosed in the parent application, i.e., U.S. Appl. No. 14/118,254.
English language translation of Mexican Office Action in foreign counterpart U.S. Appl. No. 14/118,254, the parent application, dated Jun. 6, 2017.

FIG. 3
POLYISOBUTYLENE SAMPLE FROM EXAMPLE 7 SHOWING THE PRESENCE OF BHT (8.5 ppm wt) ELUTING AT 13.627 MINUTES (TOP) AND AN M/Z VALUE OF 205 (BELOW) TYPICAL OF BHT

FIG. 4

A BHT STD (6ppm) ELUTING AT 13.734 MINUTES. THE STANDARD ALSO INDICATES A CHARACTERISTIC PEAK OF BHT AT AN M/Z VALUE OF 205

PRODUCTION OF HIGHLY REACTIVE LOW MOLECULAR WEIGHT PIB OLIGOMERS

CLAIM FOR PRIORITY

This application is a divisional application based on U.S. patent application Ser. No. 14/118,254 filed Apr. 30, 2014, now U.S. Pat. No. 9,453,089. U.S. patent application Ser. No. 14/118,254 was based on PCT Application No. PCT/US2012/040897 filed Jun. 5, 2012. PCT Application No. PCT/US2012/040897 application was based on U.S. Provisional Application Ser. No. 61/520,328 filed Jun. 8, 2011 and U.S. Provisional Application Ser. No. 61/586,206 filed Jan. 13, 2012. The disclosures of the foregoing applications are incorporated herein by reference and their priorities are hereby claimed.

TECHNICAL FIELD OF THE INVENTION

The present invention relates to the preparation of polyisobutylene (PIB). In particular the present invention relates to the preparation of highly reactive, low molecular weight PIB oligomers having a relatively high degree of terminal (or alpha) unsaturation.

BACKGROUND OF THE INVENTION

The polymerization of isobutylene using Friedel-Crafts type catalysts, such as $BF_3$, is a generally known procedure which is disclosed, for example, in "HIGH POLYMERS", Vol. XXIV (J. Wiley & Sons, Inc., New York, 1971), pp. 713 ff. Reference is also made Fujisawa et al, Japan Kokai Tokkyo Koho (1994) JP 06345821 A; Faurh et al, Ger. Offen (1994) DE 4231748; Fujisawa et al, Japan Kokai Tokkyo Koho (1993) JP 05186513 A; Kuznetsova et al, U.S.S.R. (1991) SU 1659424 A1; Noda et al, European Patent Application (1991) EP 452875; Noda et al, Japan Kokai Tokkyo Koho (1988) JP 63205305 A; Sangalov et al, (1983) SU 1016304 A1; Prokofev et al, *Promyshehlennost Sintetischekogo Kauchuka* (1982) Vol. 7, 12-15; Rooney, J. *Applied Polymer Sci.* (1980) Vol. 25(7), 1365-1372; Byrikhin et al, *Lomonosova* (1975) Vol. 5(2) 107-112; Priola, *Makromolekulare Chemie* (1975) Vol. 176(7), 1969-1981; U.S. Pat. No. 3,721,661; Steigerwald, DE 2118869; and Penfold et al, *Proc. Of the Chem. Soc.* (London) (1961) 311-312. The degree of polymerization of the products obtained in these processes varies according to which polymerization technique is used. In this connection, it is to be understood that the molecular weight of the polymeric product is directly related to the degree of polymerization.

It is also known that PIB may be manufactured in at least two different grades—regular and high vinylidene. Regular grade PIB may range in molecular weight from 500 to 1,000,000 or higher, and is generally prepared in a batch process at low temperature, sometimes as low as −50 to −70° C. $AlCl_3$ or modified $AlCl_3$ is used as catalyst. The catalyst is not totally removed from the final PIB product. Molecular weight may be controlled by temperature since the molecular weight of the product varies inversely with temperature. Higher temperatures lead to lower molecular weights. Reaction times are often in the order of hours. The desired polymeric product has a single double bond per molecule, and the double bonds are mostly internal. Generally speaking, at least about 90% of the double bonds are internal and less than 10% of the double bonds are in a terminal position. Even though the formation of terminal double bonds is believed to be kinetically favored, the long reaction times and the fact that the catalyst is not totally removed, both favor the rearrangement of the molecule so that the more thermodynamically favored internal double bond isomers are formed. Regular PIB may be used as a viscosity modifier, particularly in lube oils, as a thickener, and as a tackifier for plastic films and adhesives. PIB can also be functionalized to produce intermediates for the manufacture of detergents and dispersants for fuels and lube oils.

High vinylidene PIB is characterized by a large percentage of terminal double bonds, typically greater than 70% and preferentially greater than 80%. This provides a more reactive product, compared to regular PIB, and hence this product is also referred to as highly reactive PIB. The terms highly reactive (HR-PIB) and high vinylidene (HV-PIB) are synonymous. The basic processes for producing HV-PIB include a reactor system, employing $BF_3$ and/or modified $BF_3$ catalysts, such that the reaction time can be closely controlled and the catalyst can be immediately neutralized once the desired product has been formed. U.S. Pat. No. 5,068,490 describes a process for preparing highly reactive polyisobutylene using $BF_3$ etherate complex as the catalyst. Since formation of terminal double bonds is kinetically favored, short reactions times favor high vinylidene levels. The reaction is quenched, usually with an aqueous base solution, such as, for example, $NH_4OH$, before significant isomerization to internal double bonds can take place. Number average molecular weights (Mn) of about 950-1050 is the most common product. Conversions, based on isobutylene, are kept at 75-85%, since attempting to drive the reaction to higher conversions reduces the vinylidene content through isomerization.

While such conventional processes provide good yields of high molecular weight PIB, it is quite difficult to consistently obtain molecular weights (Mn) in the low numbers such as, for example, under 1000. It is still more difficult to obtain even lower, e.g. under 800, or under 500, or even under 300 by using such processes. Attempts to produce PIB in the lower range (e.g., under Mn of 800) usually leads to loss of reactor control during production. The only option left with operators is to control the PIB reactors in manual mode i.e. switching the catalyst pumps to manual flow rather than using traditional feedback control to adjust catalyst flow sensing the reactor temperature. This usually leads to a difficult control situation and a high amount of 'off-spec' PIB product i.e. not meeting molecular weight, polydispersity or flash point constraints.

The usual method for controlling the molecular weight involves increasing the temperature of the reactor to a certain set point, and maintaining a constant chiller temperature. As reactor temperature increases, the $\Delta T$ between the reactor and the chiller temperature increases causing the conversion to increase. The higher the reactor temperature, the lower will be the molecular weight. The decrease in molecular weight can usually be attributed to a combination of chain transfer to monomer and termination reactions. A linear relationship is usually obtained when log Mn is plotted against the reciprocal of temperature (Arrhenius plot). At a constant chiller temperature, the following relationship holds:

$$\log M_n \, \alpha \frac{1}{T_r} \, \alpha \frac{1}{\text{Conversion}}$$

Therefore temperature is the most important parameter in controlling molecular weight. The reactor temperature is controlled to the set point by employing feedback control i.e. by sensing the reactor temperature and then controlling the initiator feed rate to the reactors. For producing certain very low molecular weights (typically below 700 to 800 Mn), the reactor temperature set-points need to be set very high. The higher reactor temperatures result in conversions reaching 100% because of the large difference between reactor and chiller temperatures. At such a stage the usual feedback control logic of manipulating the initiator flow rate to control temperature does not hold. This results in a loss of control of the reaction making it very difficult to consistently produce low molecular weight PIB polymers within the desired specifications (Mn, PDI and viscosity and flash point).

U.S. Pat. No. 5,962,604 describes a process for preparing low molecular weight, highly reactive polyisobutylene using $BF_3$ as the catalyst. The process is conducted in at least two stages.

U.S. Pat. No. 6,683,138 describes a process for preparing highly reactive polyisobutylene using $BF_3$ as the catalyst.

U.S. Pat. No. 5,556,932 describes a process for preparing chlorine-free, non-drying isobutene-diene copolymers using $BF_3$ as the catalyst.

EP 0154164 describes a process for preparing polyisobutylene using $BF_3$ as the catalyst, ethylene as solvent and 2,4,4-trimethyl-1-pentene containing less than 1% by weight foreign constituents.

Highly reactive PIB oligomers with Mn under 1000 are useful as, for example, drilling fluid additives, precursors for specialty surfactants, viscosity modifiers and the like. It is, therefore, useful to find a manufacturing process to consistently obtain such oligomers without significant loss of control or economics.

SUMMARY OF THE INVENTION

In one embodiment, the present invention is the discovery of a liquid phase polymerization process for isobutylene to manufacture highly reactive PIB oligomers having Mn under 1000, preferably under 800, more preferably under 500 and still more preferably under 300, using a catalyst composition comprising a Friedel-Crafts catalyst and a complexing agent, in the presence of a chain transfer agent ("CTA"). The process advantageously uses short residence times, for example, under 4 minutes, for the isobutylene in the polymerization reaction zone. PDI values for the inventive products are preferably less than 2, most preferably from 1.1 to 1.5.

In another embodiment there is provided a polyisobutylene composition having Mn under 1000 exhibiting a multimodal molecular weight distribution, at least 70% terminal double bonds and a polydispersity under 2.0 prepared using a low molecular weight chain transfer agent, characterized in that the composition exhibits a low molecular weight relative maximum in its molecular weight distribution corresponding to the presence of said chain transfer agent.

In yet another embodiment, there is provided a reactive low molecular weight polyisobutylene composition comprising at least 50 mol percent alpha vinylidene terminated polyisobutylene molecules, the composition having a polydispersity of no more than 1.5 and a number average molecular weight of at least 500 Daltons and no more than 1000 Daltons.
mposition.

In still yet another embodiment there is provided a liquid phase polymerization process to manufacture polyisobutylene (PIB) having a number average molecular weight, Mn, of 1000 Daltons or less and at least 50 mol % percent alpha vinylidene terminated polyisobutylene molecules, the process including: a) providing a feedstock comprising isobutylene; b) providing a catalyst composition comprising a Friedel-Crafts catalyst and a complexing agent therefor; c) providing a suitable chain transfer agent ("CTA"); d) providing a polymerization-retarding agent; e) introducing said feedstock, said catalyst composition, said chain transfer agent and said polymerization-retarding agent into a reaction zone to form a reaction mixture; f) intimately intermixing the reaction mixture in said reaction zone; g) optionally adding a modifier; h) maintaining the reaction mixture in its intimately intermixed condition to thereby cause the isobutylene therein to undergo polymerization to form polyisobutylene; and i) withdrawing a product stream comprising low molecular weight, highly reactive polyisobutylene from said reaction zone.

Still further features and advantages will become apparent from the discussion which follows.

BRIEF DESCRIPTION OF THE DRAWINGS

The present invention is described in connection with the attached Figures wherein.

DETAILED DESCRIPTION OF THE INVENTION

The invention is described in detail below with reference to several embodiments and numerous examples. Such discussion is for purposes of illustration only. Modifications to examples within the spirit and scope of the present invention, set forth in the appended claims, will be readily apparent to one of skill in the art. Terminology used throughout the specification and claims herein is given its ordinary meaning for example, psi refers to pressure in lbs/inch$^2$ and so forth. Terminology is further defined below.

Percent, percent, % or like terminology refers to mole percent unless otherwise indicated.

Unless otherwise specified, molecular weight herein is reported as number average molecular weight, in Daltons, and is measured by gel permeation chromatography (GPC). GPC measurements may be carried out using a Viscotek GPCmax® instrument (Malvern instruments, Worcestershire, UK) employing a 3-column set-up (5 μm (particle size) 100 Angstrom (pore size), 5 μm 500 Angstrom, 5 μm 10$^4$ Angstrom) and a Refractive Index (RI) detector. Polyisobutylene standards are used to construct the calibration curve using this technique.

Polydispersity or PDI is defined as the ratio of the weight average molecular weight divided by the number average molecular weight of the polymer.

Polyisobutylene, "PIB" and like terminology refers to polymers made up of repeat units derived from isobutene, also referred to as isobutylene.

Such polymers are derived from feedstocks made up of purified isobutenes and hydrocarbon diluents, from isobutene concentrate, dehydro effluent, or from raffinate streams. The PIB polymer consists essentially of repeat units derived from isobutylene, but may contain minor amounts of material derived from 1-butenes, butadiene or other $C_4$ olefins, 2-butenes (cis and/or trans) depending on the feedstock composition. Typically, the polymer is more than 99% by weight derived from isobutylene monomer. One of skill in the art will appreciate that the feedstock may need to be purified to remove water and oxygenates such as alcohols, ethers and so forth to avoid adverse effects on the catalyst. Typical media for removal of impurities from hydrocarbon feed streams use molecular sieves, activated alumina and other hybrid adsorbents. A suitable absorbent to reduce water and oxygenate levels to desired limits is UOP AZ 300 (Des Plaines, Ill., USA). Post treatment, prior to feeding to the reactor, the feed stream preferably has less than 3 ppm of oxygenates and less than 1 ppm of water.

Structures of Double Bonds in Olefinic Polyisobutylenes

The following major end groups have been commonly identified in PIB structures having mid-range and high vinylidene content PIB. See, for example, W. Gunther et al, *Die Angewandte Makromoleculare Chemie*, Vol. 234 (1996), pages 71-90; and J. Spevacek et al, *Polymer Bulletin*, Vol. 34 (1995), pages 461-467.

The numbers in Table 2 in this Description indicate a certain type of end-group as a percentage of the sum of all the PIB end-groups (aliphatic and olefinic) of the composition. The end-groups not identified as any of the above, are summed up as 'other' in Table 2. When calculating endgroup percentages, all PIB molecules found in the PIB compositions having a significant presence (more than half a percent or so) are included in endgroup calculations. The end group content is determined by nuclear magnetic resonance $^{13}C$ NMR as is well known in the art.

A polyisobutylene composition as that term is used herein includes dimers as well as any residual chain transfer agent(s) such as α-DIB and β-DIB and mixtures thereof as described hereinafter.

In one embodiment, the present invention is the discovery of a liquid phase polymerization process for isobutylene to manufacture highly reactive PIB oligomers having Mn under 1000, preferably under 800, more preferably under 500 and still more preferably under 300. In another embodiment, this invention provides a liquid phase polymerization process for isobutylene to manufacture highly reactive PIB oligomers having Mn under 1000, preferably under 800, more preferably under 500 and still more preferably under 300, using a catalyst composition comprising a Friedel-Crafts catalyst and a complexing agent, in the presence of a chain transfer agent ("CTA"). The process advantageously uses short residence times, for example, under 4 minutes, for the isobutylene in the polymerization reaction zone.

The present invention provides an improved liquid phase process for the efficient and economical production of PIB. In accordance with the invention, an isobutylene-containing feedstock stream is contacted in a reaction zone with a catalyst composition which facilitates the polymerization reaction. A CTA is provided which facilitates in producing low molecular weight oligomers of PIB. Appropriate reaction conditions are provided in the reaction zone. After an appropriate residence time, a PIB containing product stream is withdrawn from the reaction zone.

The addition of a CTA results in lower molecular weights—it is usually considered a disadvantage in producing higher molecular weight polymers. However, the inventors have advantageously used CTAs to reduce conversion (thus helping with control) as well as the molecular weight, while at the same time maximizing the alpha vinylidene content in the polymer produced. Thus, the present invention provides an improved and surprisingly advantageous process to produce PIB of low molecular weight and high reactivity.

Applicants have also found that the use of a CTA surprisingly facilitates the production of low molecular weight, highly reactive PIB in the polymerization reaction and that a polymerization-retarding agent used with the chain transfer agent greatly reduces polydispersity, leading to much better molecular uniformity.

The improved process of the present invention features the use of a Friedel-Crafts catalyst which is complexed with a complexing agent which appropriately alters the performance of the catalyst. Many useful Friedel-Crafts catalysts are known to those of ordinary skill in the related art field. In particular, many useful catalysts are described in the prior patents referenced above. Useful Friedel-Crafts catalysts include, for example, $BF_3$, $AlCl_3$, $TiCl_4$, $BCl_3$, $SnCl_4$ and $FeCl_3$ and the like.

The complexing agent for the catalyst, and in particular for the $BF_3$ catalyst, may be any compound containing a lone pair of electrons, such as, for example, an alcohol, an ester or an amine. For purposes of the present invention, however, the complexing agent may be an alcohol, desirably a primary alcohol, preferably a C1-C8 primary alcohol (such as, for example, methanol, ethanol, propanol, isopropanol, hexyl alcohol and the like) and ideally methanol.

The molar ratio of $BF_3$ to complexing agent in the catalyst composition is generally in the range of from approximately 0.5:1 to approximately 5:1 respectively, desirably within the range of from approximately 0.5:1 to approximately 2:1, and preferably within the range of from approximately 0.5:1 to approximately 1:1. Ideally, the catalyst composition may simply be a 1:1 complex of BF$_3$ and methanol. In some preferred embodiments of the invention, the molar ratio of BF$_3$ to complexing agent in said complex may be approximately 0.75:1.

The temperature in the reaction zone may generally and preferably be in the range 20-110° F., preferably in the range 40-100° F. and still more preferably in the range 70-100° F. The reactor residence time may generally be less than 4 minutes, preferably less than 3 minutes and more preferably under 2 minutes. Generally speaking, the amount of the BF$_3$ catalyst introduced into the reaction zone is within the range of from about 0.1 to about 10 millimoles for each mole of isobutylene introduced into the reaction zone. Preferably, the BF$_3$ catalyst may be introduced at a rate of about 0.5 to about 5 millimoles per mole of isobutylene introduced in the feedstock. More preferably, the BF$_3$ catalyst may be introduced at a rate of about 0.5 to about 5 millimoles per mole of isobutylene introduced in the feedstock.

Applicants found that the use of a CTA surprisingly facilitates the production of low molecular weight, highly reactive PIB in the polymerization reaction. Suitable CTAs are known in literature. For example, J. P. Kennedy et al, *Carbocationic Polymerization* (1982), page 229, John Wiley & Sons, New York, list several chain transfer agents and their transfer coefficients. A suitable CTA for the present reaction is selected from the group consisting of 2,4,4-Trimethyl-1-pentene ("α-DIB"), 2.4.4.-Trimethyl-2-pentene ("β-DIB"), 2-ethyl-1-hexene, 2-methyl-1-pentene and mixtures thereof. Of these, α-DIB, β-DIB, or mixtures thereof are preferred. The structures of α-DIB and β-DIB are shown below:

2,4,4-trimethylpent-1-ene (α-DIB)     2,4,4-trimethylpent-2-ene (β-DIB)

A "low molecular weight chain transfer agent" refers to a chain transfer agent having a molecular weight lower than M$_n$ of a polyisobutylene composition in which it resides. Typically, such transfer agents have M$_n$ of 100 to 150 Daltons and exhibit a peak corresponding to their molecular weight.

The inventive polymerization can advantageously be performed using convention equipment such as, for example, a loop reactor. Such equipment is used in conventional processes for the production of polyisobutylene. Thus, the present invention can be practiced with practically no change in the equipment used.

Yet another advantage of the present invention is the absence of inert diluents in the process. In conventional polymerizations of isobutylene, inert diluents such as an alkane (e.g., isobutane, n-butane and the like) are used. The inert diluent has to be separately removed at the end of the polymerization reaction. The absence of inert diluents in the process makes the additional separation step easier thus significantly improving the economics. The CTA in the process is generally used in excess amounts thereby functioning as a reactive diluent in those cases.

Applicants also noted that the optional use of a suitable modifier with the CTA sometimes helps in keeping the molecular weight of the PIB produced low. The purpose of the modifier is believed to assist in controlling the vinylidene content of the PIB product. The catalyst modifier may be any compound containing a lone pair of electrons such as, for example, an alcohol, ester, amine and the like. Suitable modifiers in the present invention are alcohols, preferably a C1-C8 primary alcohol, more preferably methanol.

Applicants found that the present process produces PIB with molecular weights in the desired low ranges and with alpha-vinylidene content exceeding 75, sometimes exceeding 80%. The PIB has viscosities in low ranges (e.g., between 2-80 cps at 100° F.), with flash temperatures as measured by the Pensky-Martens Closed Cup test (PMCC) in the range 100-180° F. The flash temperatures as measured by the Cleveland Open Cup test (COC) were in the range 80-150° F.

In another embodiment, the present invention discloses PIB with low molecular weight (Mn under 1000), low viscosity and PDI under 2, over 80% alpha vinylidene content with multimodal distribution, prepared by the presently described process.

In one aspect of the invention, there is provided a reactive low molecular weight polyisobutylene composition comprising at least 50 mol percent alpha vinylidene terminated polyisobutylene molecules, the composition having a polydispersity of no more than 1.5 and a number average molecular weight of at least 500 Daltons and no more than 1000 Daltons prepared with both a CTA and a polymerization-retarding reagent.

Without intending to be bound by any particular theory, it has been well known that nonnucleophilic strong bases such as hindered pyridine compounds called 'proton traps' are used in carbocationic polymerization systems to eliminate initiation by protic impurities. Electron donor (ED) compounds such as dimethyl acetamide (DMA), dimethysulfoxide (DMSO) or pyridines are also added to reduce the iconicity (positive charge) of the active species and thus eliminate or reduce side reactions such as transfer to monomer. Thus these greatly reduce polydispersity in cationic polymerization systems and are often used to synthesize living polymers with very narrow polydispersities and well defined structures. However, these usually also result in greatly reduced rates of polymerization. EDs are also known to form complexes with the active species and these can precipitate out of the polymerization system resulting in undesirable impurities. Provided that the polymerization-retarding agent is carefully selected and/or controlled via appropriate concentration levels, the products of the invention are produced as described herein.

Desired particularly in continuous polymerization systems will be mildly basic compounds which could be used as controlled polymerization rate retarders which benefit polydispersity but at the same time do not precipitate out of the polymerization system or greatly effect reaction rate. Retarding agents are effectively used especially when the goal is to make low molecular weight polymers.

*Electron Pair Donors in Carbocationic Polymerization*, Kaszas et al., Polymer Bulletin 20, pp. 413-419 (1988); and U.S. Pat. No. 6,852,808, issued Feb. 8, 2005, entitled "Method for Producing Homopolymers and Copolymers of Isobutene", to Hüffer; the entire disclosures of which are incorporated herein by reference disclose compounds which are optionally used in connection with the present invention. Suitable polymerization electron donors, retarding and chain transfer agents for use with the invention are also described in Kennedy, J. P. and Ivan, B., DESIGNED POLYMERS BY CARBOCATIONIC MACROMOLECULAR ENGINEER- ING: THEORY AND PRACTICE, Hanser (1991), pp. 86-90 and 136-137, the disclosure of which is also incorporated herein by reference.

Polymerization retarding agents are used together with chain transfer agents to produce products of low polydispersity (polydispersity or PDI is the ratio of the weight average molecular weight divided by the number average molecular weight of the polymer). Suitable polymerization-retarding agents are compounds that have mild basicity, especially phenolic compound and hindered phenols where the retarding effect can be controlled either by the type of phenol molecule selected or its concentration in the polymerization system. (*Rates of Initiation of the Cationic Polymerization of Isobutene*, Russel et al., J. Polymer Science, Symposium No. 56, pp. 183-189 (1976);) For example, various hindered phenolic structures could be used as mild rate retarders, strong rate retarders or copolymers depending on the functionality of the phenyl ring. Some preferred polymerization-retarding agents include:

2,6-bis(1,1-dimethylethyl)-4-methylphenol (BHT)

2,6-di-tert-butylphenol or, if a polymerizable compound is preferred, a vinyl functional hindered phenol may be used such as:

2,6-di-tert-butyl-4-vinylphenol

Hindered phenol polymerization-retarding agents remain in the composition, whether or not copolymerized into the polymer backbone and are operative as antioxidants such that they stabilize the polymer in use. See *Functional Polymers, XLIII. Olefin Copolymers of 2,6-Di-t-butyl-4-vinyl (or 4-isopropenyl) phenol*, Paul Grosso and Otto Vogl, J. Macromol. Sci.-Chem., A23(11), pp. 1299-1313 (1986) as well as U.S. Pat. No. 4,097,464, issued Jun. 27, 1978, entitled 2,6-Di-Tert-Alkyl-4-Vinylphenols as Polymerizable Antioxidants", to Kline and U.S. Pat. No. 5,157,164, issued Oct. 20, 1992, entitled "Polymerizable Antioxidant Composition", to Olivier. Ethyl benzoate and other compounds may also be employed as polymerization-retarding agents to control polydispersity, such as the compounds disclosed in the following reference:

*Cationic Polymerization of Isobutylene Coinitiated by AlC13 in the Presence of Ethyl Benzoate*, Li et al., Chinese Journal of Polymer Science, Vol. 28, No. 1 (2010), pp 55-62.

Applicants found that the present process produces PIB with molecular weights in the desired low ranges and with alpha-vinylidene content exceeding 75, sometimes exceeding 80%. The PIB has viscosities in low ranges (e.g., between 2-80 cps at 100° F.), with flash temperatures as measured by the Pensky-Martens Closed Cup test (PMCC) in the range 100-180° F. The flash temperatures as measured by the Cleveland Open Cup test (COC) were in the range 80-150° F.

The products of the invention may be made in a loop reactor. Further details relating to the operation of such reactors are provided in PCT/US2102/040897 as well as European Patent 1 242 464, the disclosures of which are incorporated by reference.

The following examples are only illustrative and are not intended to limit the invention.

Example 1

Experiments were conducted using high purity Isobutylene (HPIB, 99.8% pure) added to a reactor loop in an apparatus of the class illustrated in PCT/US2102/040897, maintaining the total flow rate of monomer to the reactor loop at 100 mL/min. DIB was added at the desired flow rate to the reaction loop using a separate feed pump. Reactions were carried out at temperatures between 80 and 95° F. The pressure in the reactor loop was maintained at @ 200 psi. The internal diameter of the reactor tube was 0.305" and the total reactor volume was 228 cm$^3$. Flow of the BF$_3$-methanol complex was controlled using a feedback control loop such that the reaction set point was maintained. Modifier (methanol) flow was maintained at a certain ratio to the initiating species. The recirculation rate in the reactor loop was 2 gpm.

Molecular weight measurements were made using size exclusion chromatography (SEC) using PIB standards. The alpha analysis was conducted using GC.

I. Runs without Methanol Modifier

Example 1

Comparing the Use of a Chain Transfer Agent with that of Isobutane

Experiments without modifier (MeOH) were conducted with a mixture of alpha-DIB (80%) and beta-DIB (20%). Run 1 was a comparative experiment using the conventional solvent isobutane as the diluent with no chain transfer agent. Run 2 used chain transfer agent DIB and no isobutane (diluent). The results are as shown in Table 1. At 90° F., the poly(isobutylene) product in Run 1 had a Mn of 1505 and a viscosity of 480 cP. Comparative run 2 with DIB instead of Isobutane had a much lower Mn and viscosity.

TABLE 1

| Run | Reactor Temp (F) | Chiller Temp (F) | Solvent (wt %) | BF3:MeOH Ratio | Mn | PDI | Viscosity (cP) | Flash (F) PMCC/COC |
|---|---|---|---|---|---|---|---|---|
| 1 | 90 | 40 | 7 | 1:1 | 1505 | 2.02 | 480.3 | 234/158 |
| 2 | 90 | 20 | 6 | 1:1 | 1056 | 1.76 | 262.5 | 232/164 |
| 3 | 83 | 40 | 6 | 0.6:1 | 600 | 1.73 | 28.2 | 156/134 |
| 4 | 85 | 40 | 6 | 0.56:1 | 448 | 1.35 | 9.15 | 134/110 |
| 5 | 90 | 40 | 6 | 0.56:1 | 315 | 1.16 | 2.94 | 110/94 |
| 6 | 95 | 40 | 6 | 0.56:1 | 305 | 1.10 | — | 104/86 |

It can be seen that the addition of a chain transfer agent leads to greatly reduced molecular weight without manipulating temperature. Without using additional methanol as modifier, the alpha vinylidene of the product synthesized using DIB is about 54% which is approximately in the range of product synthesized using isobutane as a diluent. As shown in Table 1, the flash temperatures in Runs 1 and 2 were also in the range of products synthesized using isobutane as a diluent.

II. Runs with MeOH Modifier

Experiments were conducted with DIB as the chain transfer agent and methanol added separately as a modifier to increase the alpha content. Runs 3 thru 6 (Table 1) were conducted with additional methanol added as a modifier to increase the alpha content. As shown in Table 1, the synthesized poly(isobutylene) oligomers were in the Mn range between 250 and 650, and a viscosity range between 2-40 cps at 100° F. The alpha content of the PIB as measured by NMR was in the 80 to 90% range (Table 2) with tetrasubstituted bonds less than 3%. Polydispersity (PDI) was in the 1-2 range.

Mn values were significantly lower with higher methanol flows (lower ratios). The viscosity of PIB also decreased exponentially with decreasing Mn. Thus, by appropriately adjusting the DIB flow, methanol ratio, and temperature, HR-PIB in the low viscosity range between 2 and 40 cP (at 100° C.) with Mn in the range 250-650 range could be synthesized.

Also, as shown in Table 1, the PIB exhibited flash temperatures in the range 115-180° F. as measured by the Pensky-Martens Closed Cup test (PMCC). The flash temperatures as measured by the Cleveland Open Cup test (COC) were in the range 90-130° F. Mn ranged from 300 to 600. The flash temperatures showed a linear relationship with Mn.

The PIB product was analyzed by $^{13}C$ NMR for the alpha vinylidene content as well as olefin distribution (i.e. relative amounts of trisubstituted, tetrasubstituted and other double bonds). The results for Runs 1 (Isobutane diluent), 2 (i DIB for comparison) and runs 3, 4, 5 and 6 (DIB+methanol) are shown in Table 2 for comparison.

TABLE 2

$^{13}C$ NMR Results and distribution type

| Run | Alpha | Beta | trisub | tetrasub | other | Distribution |
|---|---|---|---|---|---|---|
| 1 | 64.3 | 23.3 | 1.4 | 4.2 | 6.8 | Unimodal |
| 2 | 62.8 | 15.7 | 3.9 | 5.6 | 12 | Unimodal |
| 3 | 80.7 | 9.4 | 0.7 | 2.7 | 6.5 | Multimodal |
| 4 | 81 | 8.6 | 0.4 | 2.2 | 7.8 | Multimodal |
| 5 | 85 | 8.1 | 0.8 | 1.7 | 4.4 | Multimodal |
| 6 | 84.6 | 7.4 | 2.2 | 1 | 4.8 | Multimodal |

As can be seen, the PIB produced by the present process using a chain transfer agent and modifier exhibits multimodal distribution (versus unimodal distribution from the polymer produced by the comparative, conventional process using isobutane). By appropriately adjusting methanol to $BF_3$ ratio (i.e. regulating methanol flow), an alpha vinylidene content of greater than 80% can be obtained. It was also noted that tetramer content was less than 3%.

Figure 1:
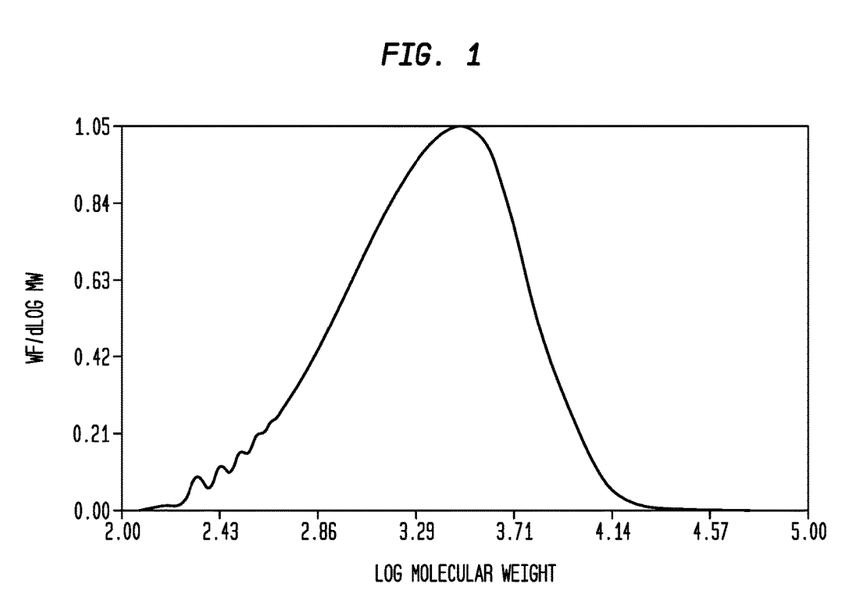
FIG. 1 and FIG. 2 show differential molecular weight distribution curves for the product PIB produced by the inventive reaction.
Figure 2:
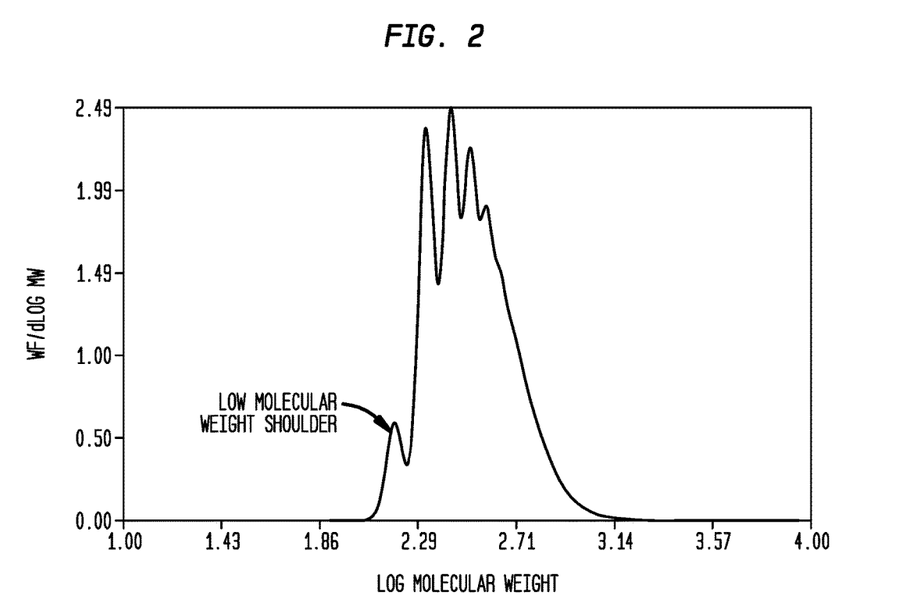

FIGS. 1 and 2 indicate differential molecular weight distribution curves. The frequency of the weight fraction is plotted along the y-axis with the log (molecular weight) plotted along the x-axis. It can be noted that FIG. 1 shows a unimodal distribution whereas FIG. 2 shows a multimodal distribution. It can also be noted that at the left extremity of the spectrum, a prominent low molecular weight shoulder (relative maximum) corresponding to the added dimer (molecular weight of approximately 112) can be seen. The area of this peak varies depending on the added amount of dimer (CTA) and can range from 2 to 20% or in a narrower range from 4 to 10% of the polyisobutylene composition.

Experimental Procedure Examples 7, 8

Production was conducted in a loop reactor as described above wherein the Isobutylene 99.95%, DIB with butylated hydroxytoluene (BHT) present at a concentration of 75 ppm in the DIB and the BF3 methanol catalyst complex were added to the reactor loop in an apparatus of the class illustrated in PCT/US2102/040897. The flow of monomer was maintained at a constant rate. The inhibited DIB was added at the desired flow rate to the reaction loop using a separate feed pump. Reactions were carried out at temperatures between 80 and 95 F. The pressure in the reactor loop was maintained at @ less than 200 psi. Flow of the BF3-methanol complex was controlled using a feedback control loop such that the reaction set point was maintained. Modifier (methanol) flow was maintained at a certain ratio to the initiating species. Molecular weight measurements were made by size exclusion chromatography (SEC) using PIB standards. BHT was calibrated using a GC-MS instrument.

A typical set of process conditions for the synthesis of a PIB product in the 600 and 450 Mn range is as shown in Table 3. Properties of the products appear in Table 4.

TABLE 3

Reactor conditions for the synthesis of low molecular weight PIB with added inhibitor

| DESCRIPTION | Example 7 600 Mn | Example 8 450 Mn | UNITS |
|---|---|---|---|
| PIB REACTOR FEED | 24 | 38 | GPM |
| DIB CONCENTRATION | 15 | 12 | WT % |
| INHIBITOR (BHT) IN DIB | 75 | 75 | PPM |

TABLE 3-continued

Reactor conditions for the synthesis of low molecular weight PIB with added inhibitor

| DESCRIPTION | Example 7 600 Mn | Example 8 450 Mn | UNITS |
|---|---|---|---|
| FEED CHILLER OUTLET TEMP | 45 | 64 | DEG F. |
| PIB REACT RECIRCULATION | 520 | 600 | GPM |
| REACTOR TEMP | 91 | 91 | DEG F. |
| INITIATOR FLOW | 43 | 85 | ML/MIN |
| MODIFIER FLOW | 14 | 39 | ML/MIN |
| CHILLER TEMPERATURE | 45 | 65 | DEG F. |
| CRUDE FLASH PREHEATER TEMP | 405 | 395 | DEG F. |
| VACUUM FLASH PRESSURE | 3.8 | 4.2 | PSIA |
| VACUUM FLASH TEMP | 405 | 400 | DEG F. |
| REACTOR CONVERSION | 96 | 85 | % |

TABLE 4

Product properties of polyisobutylene as synthesized according to reaction conditions in Table 3.

| Parameter | Example 7 | Example 8 | Unit | ASTM |
|---|---|---|---|---|
| MOLECULAR WEIGHT | 609 | 428 | Mn | |
| POLYDISPERSITY | 1.43 | 1.40 | — | |
| KINEMATIC VISCOSITY | 30.41 @ 100° C. | 67.35 @ 40° C. | cSt | ASTM D-445 |
| FLASH POINT, COC | 155 | 120 | ° C. | ASTM D-92 |
| SPECIFIC GRAVITY @ 15.6° C./15.6° C. | 0.8747 | 0.8567 | — | ASTM D-4052 |
| COLOR | 8 | 7 | Pt—Co | ASTM D-1209 |
| HAZE, PHOTOMETRIC | 0.319 | 0.258 | NTU | ASTM D-6181 |
| ALPHA VINYLIDENE | 67.78 | 70 | % | |
| APPEARANCE | CLEAR AND BRIGHT | CLEAR AND BRIGHT | | |

Figure 3:
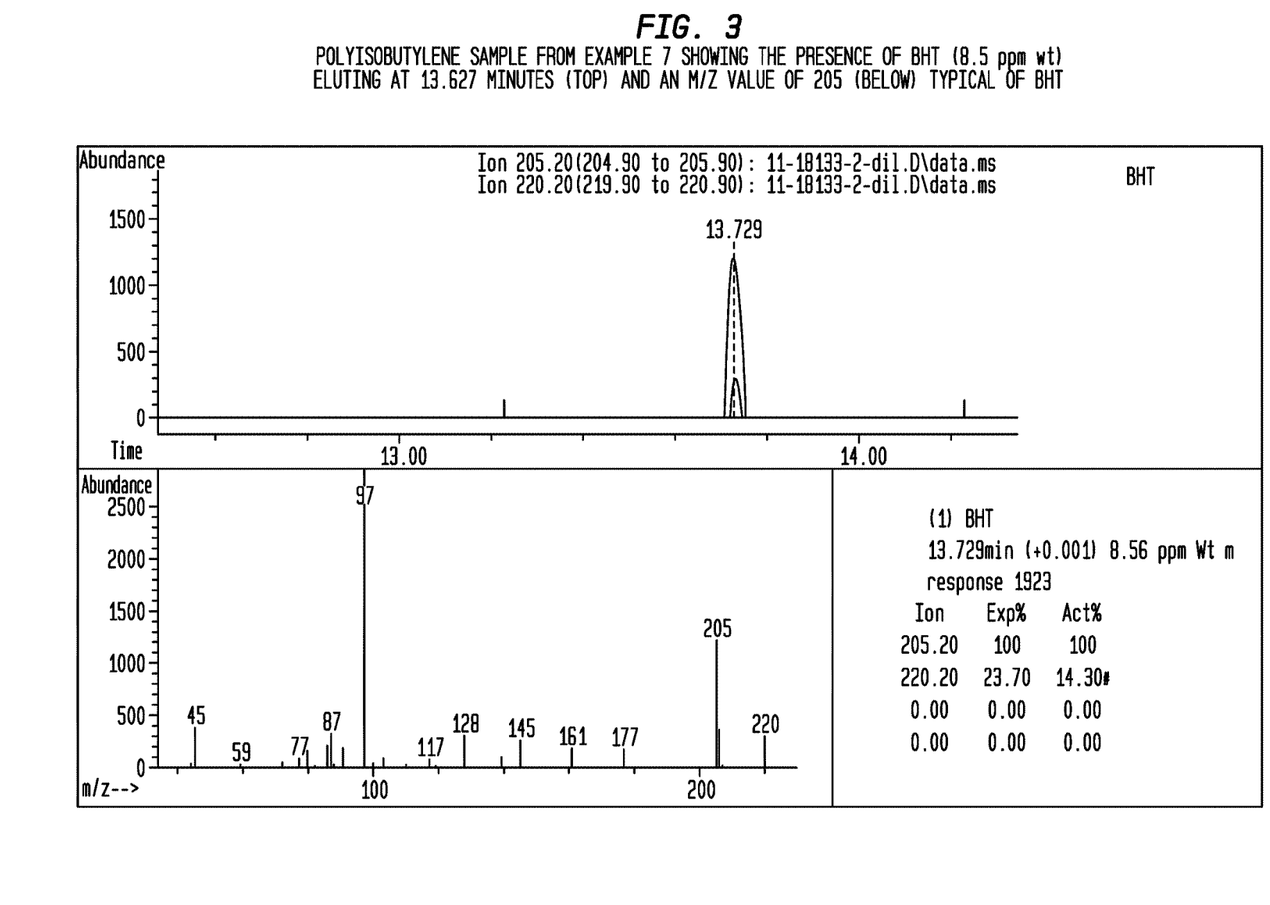
FIGS. 3 and 4 indicate GC-MS spectra for the polyisobutylene sample of example A and a BHT standard. The BHT concentration was measured at 8.56 ppm in the final PIB product and at 6 ppm in the standard. The GC-MS spectra were obtained by a GC-MS instrument using a high polarity DB-WAX GC column.
Figure 4:
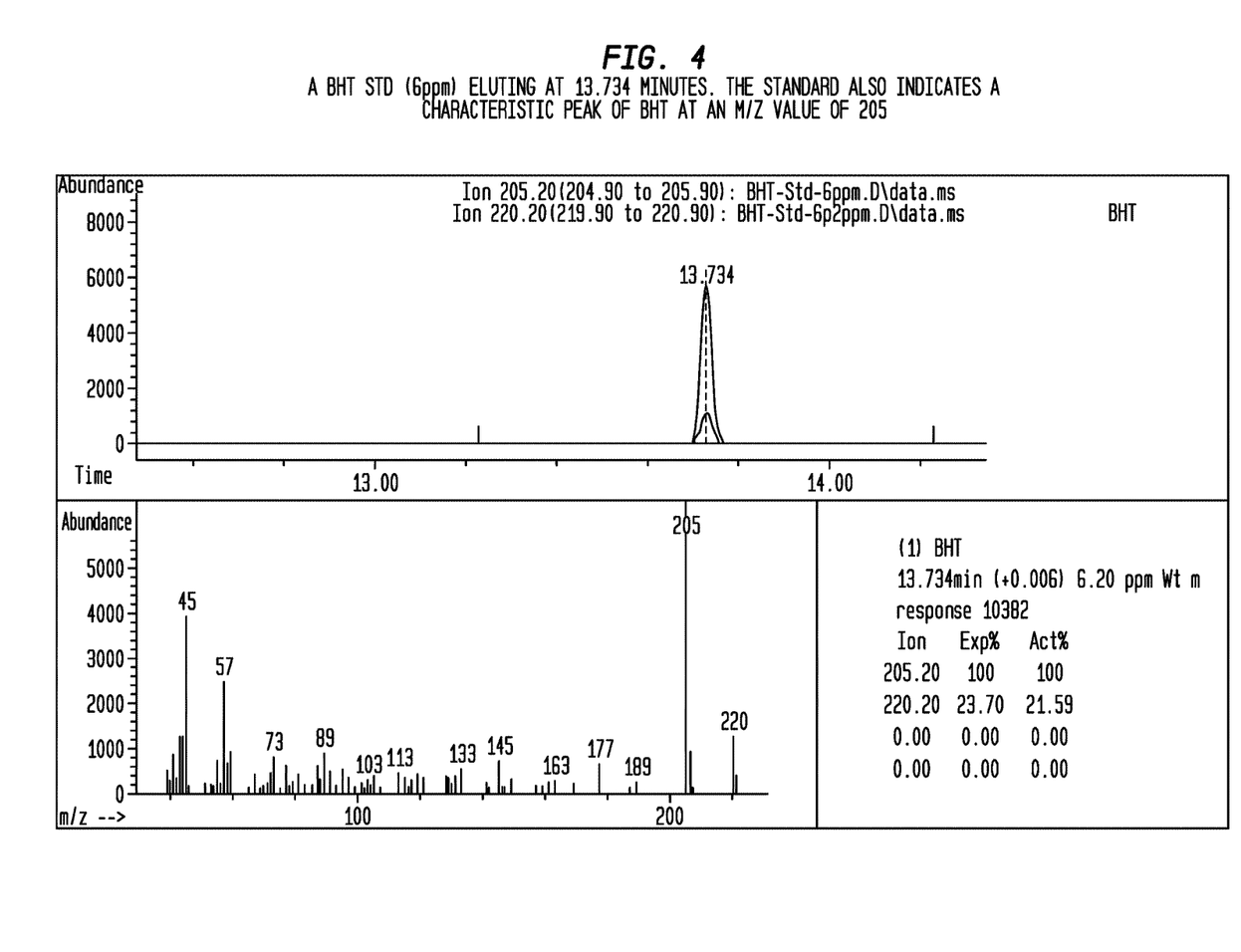

FIG. 3 and FIG. 4 indicate GC-MS spectra for the polyisobutylene sample of example 7 and a BHT standard. The BHT concentration was measured at 8.56 ppm in the final PIB product and at 6 ppm in the standard. The GC-MS spectra were obtained by a by a GC-MS instrument using a high polarity DB-WAX GC column.

The invention material prepared with a BHT polymerization-retarding agent was prepared and compared with a like material prepared without BHT in the reaction medium. Samples were tested on a BYK Gardner instrument in accordance with ASTM 1209 for color before and after thermal aging in an oven under nitrogen for 2 weeks at 120° C. Results were as follows:

TABLE 5

Heat Aging Results

| Sample | Color # before Heat Aging | Color # after Heat Aging |
|---|---|---|
| PIB with BHT retarding agent | 8 (Mn 609, PDI 1.43) | 30 (Mn 634, 1.41) |
| PIB without BHT retarding agent | 14 (Mn 637, PDI 1.59) | 50 (Mn 674, 1.57) |

As can be seen in Table 5, the compositions prepared with polymerization-retarding agent exhibited unexpectedly superior color both before and after heat aging.

Additional Embodiments

There is thus provided a liquid phase polymerization process of isobutylene to manufacture highly reactive polyisobutylene (PIB) having Mn under 1000 and at least 70% terminal double bonds, said process includes: a) providing a feedstock comprising isobutylene; b) providing a catalyst composition comprising a Friedel-Crafts catalyst and a complexing agent therefor; c) providing a suitable chain transfer agent ("CTA"); d) introducing said feedstock, said catalyst composition and said chain transfer agent into a reaction zone to form a reaction mixture; e) intimately intermixing the reaction mixture in said reaction zone; f) optionally adding a modifier; g) maintaining the reaction mixture in its intimately intermixed condition and keeping it at a temperature of about 20-110° F. in the reaction zone, to thereby cause the isobutylene therein to undergo polymerization to form polyisobutylene; h) withdrawing a product stream comprising low molecular weight, highly reactive polyisobutylene from said reaction zone; and i) optionally controlling the introduction of said feedstock into said reaction zone and the withdrawal of said product stream from the reaction zone such that the residence time of the isobutylene undergoing polymerization in the reaction zone is no greater than about 4 minutes. In many cases, the PIB has molecular weight under 800, under 500 or under 300.

The Friedel-Crafts catalyst is selected from the group consisting of $BF_3$, $AlCl_3$, $TiCl_4$, $BCl_3$, $SnCl_4$ and $FeCl_3$, and the complexing agent is typically an alcohol such as a primary alcohol, notably methanol. The modifier is optionally present and is typically an alcohol and may be methanol as well.

The CTA may be selected from the group consisting of 2,4,4-Trimethyl-1-pentene ("α-DIB"), 2.4.4.-Trimethyl-2-pentene ("β-DIB"), 2-ethyl-1-hexene, 2-methyl-1-pentene and mixtures thereof. One preferred embodiment is wherein said CTA is a mixture of α-DIB and β-DIB in an 80:20 molar ratio.

The PIB produced may have at least 75% terminal double bonds or at least 80% terminal double bonds. One preferred embodiment is wherein the PIB has Mn under 1000 and at least 75% terminal double bonds and another is wherein the PIB has Mn under 500 and at least 75% terminal double bonds. Still yet another embodiment is wherein the PIB has Mn under 300 and at least 75% terminal double bonds.

The catalyst and complexing agent may be present in a molar ratio of about 0.3:1 to about 5:1 or the catalyst and complexing agent are present in a molar ratio of about 0.5:1 to about 2:1. A preferred mixture is wherein the catalyst and complexing agent are present in a molar ratio of about 0.5:1 to about 1:1. Typically, from about 0.1 to about 10 millimoles of $BF_3$ are used in the catalyst composition for each mole of isobutylene introduced into the reaction. In some cases, from about 0.5 to about 5 millimoles of $BF_3$ are used in the catalyst composition for each mole of isobutylene introduced into the reaction and in others about 0.5 to about 2 millimoles of $BF_3$ are used in the catalyst composition for each mole of isobutylene introduced into said reaction.

The polydispersity of the polyisobutylene is no more than about 2.0 in most embodiments and typically between 1 and 2; preferably, the polydispersity of said polyisobutylene no more than about 1.65 and in preferred cases from 1.1 to 1.5 or from 1.1 to 1.4.

The polymerization is preferably conducted in a loop reactor in accordance with the present invention. One preferred product has Mn under 800 and at least 70% terminal double bonds. Another preferred product has Mn under 500 and at least 70% terminal double bonds. Still another preferred product has Mn under 300 and at least 70% terminal double bonds. Still yet another preferred product has Mn under 1000 and exhibits a multimodal molecular weight distribution, at least 70% terminal double bonds and a polydispersity under 2.0. The present invention is thus generally directed to a continuous reaction in a loop reactor preferably operated at recirculation to feed ratios of from 20 to 100 or so, typically from 25 to 80 and in some cases from 25 to 50.

In another embodiment, there is provided a polyisobutylene composition having Mn under 1000 exhibiting multimodal distribution, at least 70% terminal double bonds and a polydispersity under 2.0 prepared using a low molecular weight chain transfer agent, characterized in that the composition exhibits a low molecular weight relative maximum in its molecular weight distribution corresponding to the presence of said chain transfer agent, preferably the chain transfer agent is present at a content of from 2 weight percent to 20 weight percent of the composition. The composition may be characterized in some cases in that the composition exhibits a low molecular weight relative maximum in its molecular weight distribution corresponding to the presence of said chain transfer agent at a content of from 4 weight percent to 10 weight percent of the composition. Typically, such transfer agents have a molecular weight of 100 to 150 Daltons and exhibit a peak corresponding to their molecular weight. Preferably, the polydispersity of the composition is no more than about 1.65 and most preferably the polydispersity of the composition is from 1.1 to 1.5 or from 1.1 to 1.4.

Another embodiment provides a reactive low molecular weight polyisobutylene composition comprising at least 50 mol percent alpha vinylidene terminated polyisobutylene molecules, the composition having a polydispersity of no more than 1.5 and a number average molecular weight of at least 500 Daltons and no more than 1000 Daltons.

In some cases the reactive low molecular weight polyisobutylene composition comprises at least 60 mol percent alpha vinylidene terminated polyisobutylene molecules and in others at least 70 mol percent alpha vinylidene terminated polyisobutylene molecules. In most cases, the reactive low molecular weight polyisobutylene composition comprises from 50 to 99 mol percent alpha vinylidene terminated polyisobutylene molecules and the compositions are characterized in that no more than 10 mole % of the PIB molecules of the composition have tetra-substituted double bonds, more preferably wherein no more than 5 mole % of the PIB molecules of the composition have tetra-substituted double bonds. The reactive low molecular weight polyisobutylene compositions preferably have a polydispersity of no more than 1.4, more preferably no more than 1.3 and suitably from 1.2 to 1.5. In some cases, from 500 Daltons to 900 Daltons and in others a number average molecular weight of from 500 Daltons to 750 Daltons and in others a number average molecular weight of from 550 Daltons to 675 Daltons. The composition optionally further includes a polymerization-retarding agent such as a phenolic compound which may be a hindered phenol such as 2,6-bis(1,1-dimethylethyl)-4-methylphenol (BHT)

In some embodiments, a reactive low molecular weight polyisobutylene composition includes a polymerization-retarding agent copolymerized with isobutylene. The polymerization-retarding agent copolymerized with isobutylene in the polyisobutylene composition may be operative as an antioxidant. The reactive low molecular weight polyisobutylene composition may include a polymerization-retarding agent copolymerized with isobutylene in the polyisobutylene composition which is a hindered phenol compound such as a vinyl functional hindered phenol compound. In still other cases, the reactive low molecular weight polyisobutylene composition includes a polymerization-retarding agent copolymerized with isobutylene in the polyisobutylene composition which is a vinyl hindered phenol compound of the formula:

2,6-di-tert-butyl-4-vinylphenol

The polymerization-retarding agent may be present in an amount of from 1 to 3000 ppm by weight of the polyisobutylene composition, suitably the polymerization-retarding agent is present in an amount of from 1 to 1000 ppm by weight of the polyisobutylene composition and preferably the polymerization-retarding agent is present in an amount of from 5 to 500 ppm by weight of the polyisobutylene composition; and even more preferably the polymerization-retarding agent is present in an amount of from 10 to 100 ppm by weight of the polyisobutylene composition.

Still another embodiment is directed to a liquid phase polymerization process to manufacture polyisobutylene (PIB) having a number average molecular weight, Mn, of 1000 Daltons or less and at least 60 mol % percent alpha vinylidene terminated polyisobutylene molecules, said process comprising: a) providing a feedstock comprising isobutylene; b) providing a catalyst composition comprising a Friedel-Crafts catalyst and a complexing agent therefor; c) providing a suitable chain transfer agent ("CTA"); d) providing a polymerization-retarding agent; e) introducing said feedstock, said catalyst composition, said chain transfer agent and said polymerization-retarding agent into a reaction zone to form a reaction mixture; f) intimately intermixing the reaction mixture in said reaction zone; g) optionally adding a modifier; h) maintaining the reaction mixture in its intimately intermixed condition to thereby cause the isobutylene therein to undergo polymerization to form polyisobutylene; and i) withdrawing a product stream comprising low molecular weight, highly reactive polyisobutylene from said reaction zone. The PIB suitably has a number average molecular weight, Mn, under 800 Daltons, under 700 Daltons; suitably from 300 Daltons to 1000 Daltons. The Friedel-Crafts catalyst may be selected from the group consisting of $BF_3$, $AlCl_3$, $TiCl_4$, $BCl_3$, $SnCl_4$ and $FeCl_3$ and the complexing agent may be an alcohol such as a primary alcohol and preferably methanol. That is, preferably the modifier is present and is an alcohol, most preferably methanol. The CTA may be selected from the group consisting of 2,4,4-Trimethyl-1-pentene ("α-DIB"), 2.4.4.-Trimethyl-2-pentene ("β-DIB"), 2-ethyl-1-hexene, 2-methyl-1-pentene and mixtures thereof. In one preferred embodiment the CTA is a mixture of α-DIB and β-DIB in an 80:20 molar ratio.

While the invention has been described in detail, modifications within the spirit and scope of the invention will be readily apparent to those of skill in the art. Such modifications are also to be considered as part of the present invention. In view of the foregoing discussion, relevant knowledge in the art and references discussed above in connection with the Background of the Invention, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

What is claimed is:

1. A polyisobutylene composition having Mn under 1000 exhibiting a multimodal molecular weight distribution, at least 70% terminal double bonds and a polydispersity under 2.0 prepared using an olefinic chain transfer agent having a molecular weight, Mn, lower than that of said composition, wherein said composition is characterized in that the composition exhibits a low molecular weight relative maximum in its molecular weight distribution corresponding to the presence of said chain transfer agent.

2. The composition according to claim 1, wherein said chain transfer agent has a molecular weight, Mn, of from 100 to 150 Daltons.

3. The composition according to claim 1, wherein the polyisobutylene composition has a molecular weight, Mn, of less than 800 Daltons.

4. The composition according to claim 3, wherein the polyisobutylene composition has a molecular weight, Mn, of from 300 to less than 800 Daltons.

5. The composition according to claim 1, wherein the polyisobutylene composition has a molecular weight, Mn, of from 300 to 1000 Daltons.

6. The composition of claim 1, characterized in that the composition exhibits a low molecular weight relative maximum in its molecular weight distribution corresponding to the presence of said chain transfer agent at a content of from 2 weight percent to 20 weight percent.

7. The composition of claim 1, characterized in that the composition exhibits a low molecular weight relative maximum in its molecular weight distribution corresponding to the presence of said chain transfer agent at a content of from 4 weight percent to 10 weight percent of the composition.

8. The composition of claim 1, wherein the polydispersity of said composition is no more than about 1.65.

9. The composition of claim 1, wherein the polydispersity of said composition is from 1.1 to 1.5.

10. A reactive low molecular weight polyisobutylene composition comprising at least 50 mol percent alpha vinylidene terminated polyisobutylene molecules, the composition having a number average molecular weight of no more than 1000 Daltons and is characterized in that the composition exhibits a low molecular weight maximum in its molecular weight distribution corresponding to the presence of an olefinic chain transfer agent.

11. The reactive low molecular weight polyisobutylene composition according to claim 10, comprising at least 60 mol percent alpha vinylidene terminated polyisobutylene molecules.

12. The reactive low molecular weight polyisobutylene composition according to claim 10, comprising at least 70 mol percent alpha vinylidene terminated polyisobutylene molecules.

13. The reactive low molecular weight polyisobutylene composition according to claim 10, comprising from 50 to 99 mol percent alpha vinylidene terminated polyisobutylene molecules.

14. The reactive low molecular weight polyisobutylene composition according to claim 10, wherein no more than 10 mole % of the PIB molecules of the composition have tetra-substituted double bonds.

15. A reactive low molecular weight polyisobutylene composition comprising at least 50 mol percent alpha vinylidene terminated polyisobutylene molecules, the composition having a number average molecular weight of no more than 1000 Daltons, wherein the composition further includes a polymerization-retarding agent and is characterized in that the composition exhibits a low molecular weight maximum in its molecular weight distribution corresponding to the presence of an olefinic chain transfer agent.

16. The reactive low molecular weight polyisobutylene composition according to claim 15, wherein the polymerization-retarding agent comprises a phenolic compound.

17. The composition according to claim 15, wherein said chain transfer agent has a molecular weight, Mn, of from 100 to 150 Daltons.

18. The composition according to claim 15, wherein the polyisobutylene composition has a molecular weight, Mn, of less than 800 Daltons.

19. The composition according to claim 15, wherein the polyisobutylene composition has a molecular weight, Mn, of from 300 to less than 800 Daltons.

20. The composition according to claim 15, wherein the polyisobutylene composition has a molecular weight, Mn, of from 300 to 1000 Daltons.

* * * * *